United States Patent [19]

Tararuj et al.

[11] Patent Number: 4,940,584
[45] Date of Patent: Jul. 10, 1990

[54] FRAGRANCE ENHANCED POWDER SAMPLER AND METHOD OF MAKING THE SAME

[75] Inventors: Christopher Tararuj, Mercerville; Carl K. Schaab, Princeton Jct., both of N.J.

[73] Assignee: Webcraft Technologies, N. Brunswick, N.J.

[21] Appl. No.: 207,949

[22] Filed: Jun. 17, 1988

[51] Int. Cl.$^5$ .............................................. A61K 6/00
[52] U.S. Cl. ..................... 424/401; 106/20; 106/27; 106/28; 424/502; 427/212
[58] Field of Search .............. 424/401, 490, 63, 69, 424/502; 106/20, 27, 31, 28; 427/212

[56] References Cited

U.S. PATENT DOCUMENTS

| | | | |
|---|---|---|---|
| 4,661,388 | 4/1987 | Charbonneau | 424/401 X |
| 4,720,417 | 1/1988 | Sweeny et al. | 424/401 X |
| 4,725,495 | 2/1988 | Garbe et al. | 424/401 X |
| 4,752,496 | 6/1988 | Fellows et al. | 424/401 X |

*Primary Examiner*—Thurman K. Page
*Attorney, Agent, or Firm*—Shlesinger & Myers

[57] ABSTRACT

A cosmetic sampler has a thin dry layer of discrete fragrance enhanced powder particles removable by light finger pressure as a dry free-flowing powder. The fragrance powder layer is originally applied as a liquid slurry which is dried after application, the individual powder particles being coated and having enhanced fragrance and are readily separable from each other after removal from the substrate to which they have been applied.

9 Claims, 1 Drawing Sheet

U.S. Patent
Jul. 10, 1990
4,940,584
FIGURE 1
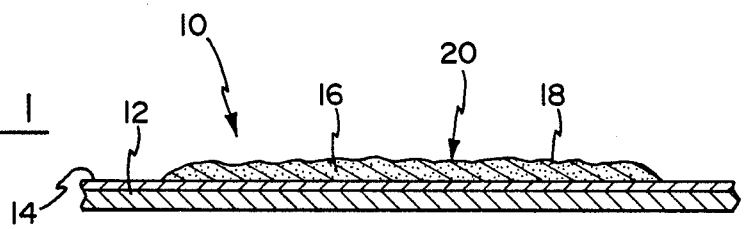
FIGURE 2
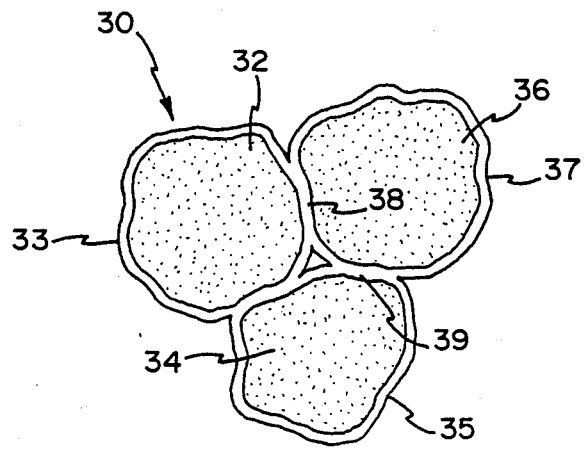
FIGURE 3
COAT FRAGRANCE POWDER WITH FRAGRANCE OIL AND HIGH MOLECULAR WEIGHT OIL
↓
MIX WITH VOLATILIZING AGENT AND BINDER
↓
APPLY TO SMOOTH SUBSTRATE SURFACE
↓
DRY FRAGRANCE POWDER LAYER
FIGURE 4
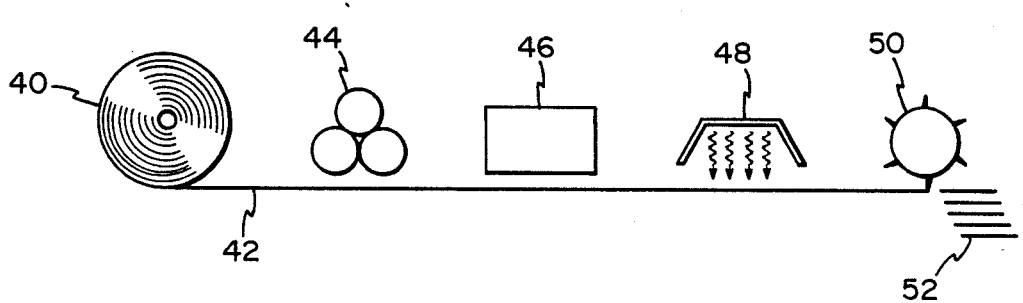

FRAGRANCE ENHANCED POWDER SAMPLER AND METHOD OF MAKING THE SAME

BACKGROUND OF THE INVENTION

This invention relates to cosmetic sampler items, and particularly to a mass produced cosmetic sampler which carries readily removable fragranced powders.

There is a growing usage and large demand for mass distributing advertising pieces which contain small samples of products, such as cosmetics. Samples are an efficient method of distributing low cost samples of products such as cosmetic blushes, lipsticks, and perfumes.

Because of the physical properties of powders, which are in a dry particulate state, it has not been possible to produce a sampler which would hold the particles or powder in position for handling and distribution purposes, and yet would, on removal, assume the free-flowing powdery characteristics of a typical powder.

SUMMARY OF THE INVENTION

Accordingly, it is a principle object of this invention to provide a sampler which can carry particulate fragranced powders which are only separable from the sampler on light finger pressure by the prospective customer.

It is a further feature of this invention to provide powders which have fragrance enhanced characteristics.

It is another feature of this invention to provide a cosmetic sampler having a readily removable fragranced powder which is closely representative of the powder being advertised.

It is a further feature of this invention to provide a cosmetic sampler which has a relatively long shelf life.

It is still a further feature of this invention to provide an effective low cost sampler item for large scale low unit costs.

It is also a feature of this invention to provide a readily appliable liquid composition containing the powder particles which can be applied by mass production techniques to a substrate, and on drying will produce a readily removable powdery layer.

These and other features and advantages of the invention will become apparent from the following description and claims.

DESCRIPTION OF THE DRAWINGS

FIG. 1 is an enlarged cross-section of a sampler section containing the dried fragrance particle layer.

FIG. 2 is an enlarged view of several treated powder particles indicating the manner in which they tend to lightly adhere to each other.

FIG. 3 illustrates the basic method steps followed in producing the dried fragrance layer.

FIG. 4 is a schematic view of a typical continuous web production technique for mass producing the sampler of FIG. 1.

Referring particularly to the drawings, FIG. 1 discloses a cross-section of a fragrance powder sampler generally indicated at 10. A substrate such as coated paper is preferably used. The samplers are produced on a mass basis with high speed printing equipment in which sampler advertising pieces are printed and formed from continuous web sheets. The powder layer is applied by printing techniques such as flexography. It may also be extruded onto particular sections of the successive advertising sampler piece blanks of the web.

The layer of removable powder, which is fragrance enhanced, is preferably applied to a smooth surface, such as that provided by coated stock. This will permit the layer to be easily removed from the sampler with light finger pressure.

The cross-section of FIG. 1 shows the paper substrate 12 which has a coated surface 14. Such paper is commercially available and the coated surface layer usually consists of a clay coating, a cellulosic or other suitable coating over the clay coating is also desirable particularly for increasing the shelf life at elevated temperature.

The fragranced powder layer 20 consists of a suspended lose mixture of fragranced powders such as talc or of commercially available fragrance powder particles. The upper surface 18 of the layer is relatively uniform. The dry powders of the layer is dry to the touch and on light contact pressure, will come off the paper as a plurality of discrete, free-flowing particles of dry powder. The consistency and color, as well as the scent will closely match an advertised commercial product which it represents. Both the powder consistency and the fragrance are closely matched.

FIG. 2 illustrates the manner in which the particles are held together in the layer. It is important that the particles have sufficient adherence to one another, so that they stick to the substrate as well as to each other during handling and distribution of the sampler items. It is also important that these particles break free of one another when light finger pressure is applied so that they assume a free flowing characteristic of the particles in a cosmetic powder or talc as commercially sold in containers.

It is also important that the fragrance of the particles when the sample layer is removed from the sampler surface of the same strength as that of a freshly opened package or container. In this respect, the sealing in of the fragrance is necessary to preclude loss of fragrance during handling and distribution of the samples. Prolonged shelf life is an important consideration.

The balancing of these two requirements is an essential aspect of this particular invention.

The three contiguous particles generally indicated at 30 in FIG. 2, illustrate the manner in which the particles are disposed in the layer 16 of FIG. 1. The fragrance oil of particles 32, 34, and 36 are supplemented by additional fragrance oil in an ordinary mixing, and then the fragrance enhanced particles are coated with a high molecular weight oil/wax such as mineral oil or cetyl palmitate to retard the volatile loss of fragrance from the particles. The mineral oil fragrance coating on the particles of FIG. 2 are indicated at 33, 35, and 37. The particles when brought into contact with one another have a tendency to loosely stick together due to the cohesiveness of the oils at abutting surfaces as indicated at 38 and 39.

The particles shown can either be ordinary talc, or a commercially available fragrance powder. Commercially available powder has approximately a 10 to 15% fragrance oil content which would be supplemented by an additional 10% by weight addition of fragrance oil. Unfragranced talc particles would have up to 25% by weight of fragrance oil added to the talc particle.

The particles are mixed with binders and a volatizing agent to produce a slurry liquid which is readily printable or extruded onto paper.

For a fragranced enhanced powder, the following constituents are preferred:

| | Fragranced Enhanced Powder |
|---|---|
| Ethyl Alcohol | 60.0 |
| Methyl Glucoside | 0.5 |
| Mineral Oil | 1.0 |
| Cetyl Palmitate | 0.5 |
| Fragrance Oil | 0.5 |
| Silica | 0.25 |
| Polysiloxane | 0.10 |
| Fragranced Powder | 36.4 |
| | 100.0 |

Where ordinary fragranced powder using a base powder such as talc is used, the following is the preferred embodiment:

| | Standard Fragranced Powder |
|---|---|
| Isopropyl Alcohol | 55.15 |
| Methyl Glucoside | 0.25 |
| Dimethicone | 1.50 |
| Isopropyl Myristate | 1.25 |
| Silica | 0.50 |
| Polysiloxane | 0.25 |
| Preservative | 0.1 |
| Fragranced Powder | 42.0 |
| | 100.0 |

The slurry mixture is prepared in either glass or stainless steel containers using commercial mixing equipment.

With respect to the formulations, there is a wide latitude in formulation percentages available. It should also be kept in mind that variations in percentage as well as additions and changes with respect to some of the ingredients will depend upon the relevant factors desired, such as better printability, aesthetics of the dried layer, fragrance character, rheology, and other factors. It is possible that a number of different percent combinations would work for a given application, but it is also possible within the limits given only one formulation would give the best results for a given finished product to be printed in a specific manner such as flexography, extrusion, etc.

A typical formulation of ingredients with the relative ranges for the type of elements is as follows for the general category of elements that make up the composition:

| | | |
|---|---|---|
| (a) | the volatizing solvent | to 84% by weight; |
| (b) | adhesion/cohesion promoters and rheological agents | 0 to 6% by weight; |
| (c) | fragrance oil | 0 to 9% by weight; (fragranced) up to 16% by weight (Unfragranced Particles) |
| (d) | rheology and processing agents | 0 to 4% by weight; |
| (e) | lubricants | 0.25 to 1.5% by weight; |
| (f) | preservatives | .05 to .10% by weight; |
| (g) | powders either fragranced or unfragranced | 15 to 50% by weight |

The solvents under (a) above include: Ethanol, isopropanol, methyl isobutyl ketone, hydrocarbon solvents, heptane, trichlorotri fluoroethane, etc.

A solvent suitable for formulation can vary according to the specific needs of a particular formulation goal or a solvent can be chosen by virtue of drying rate, flamability, or other such criteria if a specific formulation property is not required.

The ingredients under (b) above include: Methyl glucoside, mineral oils, hexylene glycol, propylene glycol, isopropyl palmitate, cetyl palmitate and other fatty alcohols, hydroxy propy cellulose and other cellulosies, etc.

This category is a combination of adhesion/cohesion promoters, color/texture enhancers, processing aids (rheological, suspension etc.) fragrance fixatives emolients, etc. Any combination of these and other suitable raw materials can be utilized to impart or enhance whatever specific qualities or characteristics are desired.

The fragrance oil (c) above) is added to import a greater initial pre-odor to the sample as well as to have more fragrance available for an extended shelf life. The oil is added with the adhesion/cohesion materials usually, but it could be withheld from the batch until the time of actual printing or it can be dry blended with the powder and then formulated with the above ingredients.

The agents under (d) above include: silicas and silicates, zinc stearate, calcium stearate etc. The adhesion/cohesion materials of item (b) are often utilized in combination with these materials to aid in rheology control, improve processing (both printing and bulk manufacturing) and to promote finished product characteristics such as longevity of fragrance, and adhesion and cohesion of the powders.

Item (e) above includes: polysiloxane, cyclomethicone, dimethyl polysiloxane etc.

Materials in this category are preferably silicone based materials which aid in manufacturing and processing by internally lubricating the system aiding mixing, pumping and overall processing. This material can be excluded however, the addition of one or more of these materials will aid overall processing.

The use of a preservative is optional.

The powders included under (g) above includes both fragranced and unfragranced powder.

Any material in a powder form can be processed by varying or modifying the formulation as necessary. This including but is not limited to bath powders, eye shadows, talcum powders etc.

FIG. 3 illustrates the broad method of the invention. As indicated above, with respect to FIG. 2, the powders are enhanced with fragrance oil and then coated.

The enhanced fragrance particles are then coated with the high molecular weight oil/wax such as mineral oil/cetyl palmitate to provide a combined seal for the fragrance essence, and a small binding function between the particles in the dried sampler layer.

Simultaneously, the fragrance enhanced particle/oil blend is mixed with a volatizing agent and a binder in the constituent formulation given above.

The next step would be the application of the liquid slurry composition to a substrate surface such as coated stock.

After application, the volatile vehicle is vaporized quickly to form the solid dried fragrance powder layer.

FIG. 4 is a schematic outline of the method as generally followed in producing samplers at high speed and low cost from a continuous web. The fragrance powder composition is applied in-line with high speed printing or extrusion equipment. The printing techniques of flexography, gravure, silk screen are printing techniques that can readily be used as part of the web fabrication technique.

The paper roll indicated at 40 in FIG. 4, provides a web 42 which is printed by passing through a printing section generally indicated schematically at 44 which prints successive cosmetic sampler blanks. A polymeric underlayer may be applied to the web in the area to be coated by the fragrance enhanced powder formulation. This underlayer may be a cellulosic or any suitable material which can be applied by standard printing techniques. The web with the printed blanks is then passed through a fragrance powder layer application section generally indicated by block 46. After receiving the thin powdered layer in liquid form, the web passes under the drying stage 48. This could be followed by several gluing stages, as well as several folding stages, but for purposes of simplicity, these additional formation stages have been omitted. The final stage is a transverse cutting stage 50 in which the web is cut transversely to separate the printed and layer containing samplers.

The viscosity of the layer as applied to the substrate is in the range of 25 to several thousand centipoises. The preferred range is from 300 to 500 centipoises.

The enhanced fragranced particles on the dried sampler due to the mineral oil/wax coating have a long shelf life of approximately 1 to 3 months depending on the formulation and fragrance oil.

The intensity of the fragrance is preserved by the coating to give a high level fragrance intensity when the layer is removed.

The formulations and process also provide a sampler with a fragrance enhanced powder layer which can readily be removed and transferred to skin. The product allows up to 100% removal, a very high pay-off of product.

The fragrance particles can be either talc (magnesium silicate) or kaolin clay (aluminum silicate) or other suitable materials or combinations thereof.

The high molecular weight coating, which is preferably mineral oil/cetyl palmitate, not only seals in the fragrance to give it a longer shelf life, but also provides some shielding with respect to the volatizing agent, if such agent is alcohol.

The percentages that are given for the two above examples, are for the constituent percentages in the slurry or a liquid applied layer. On drying the volatizing agent leaves the layer, and the percentages by weight of the dried layer will proportionately increase, reflecting the percentage loss of the volatizing agent, such as the ethyl alcohol in Example 1.

The percentages in the dried layer on the cosmetic layer, therefore, will increase proportionately such that the mineral oil and binder elements, both now functioning as a binder will have a percentage by weight, will be the sum of these two elements in the initial slurry increased by approximately 40%. The acceptable range by weight for these two elements is the percentage weight of the particle in the dried layer for the slurry of Example 1 will increase 60% and will have a range of 40 to 85%.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

What is claimed is:

1. A fragrance particle sampler, comprising:
   (a) a substrate having a smooth surface,
   (b) a layer of readily removable dry adhesively held fragranced powder particles disposed on and lightly adherent to the smooth surface of the substrate,
   (c) the particles being mixed with a large amount of fragrance oil and surface-coated with a heavy molecular weight oil/wax for sealing in the fragrance and promoting adhesion/cohesion between adjacent particles in the layer binding the particles together,
   (d) the powder particles being held temporarily in fixed position with respect to each other by the set taken by the coating on the particles binding them together,
   (e) the coating on the particles and the binding material taking a set within the layer as a residual dried layer after evaporation of the volatile liquid suspension medium originally mixed with the applied layer, whereby the particles lightly adhere to the substrate surface, and on application of light finger pressure are removable therefrom as discrete free-flowing separate particles, having the property of a fragranced powder.

2. The fragranced particle sampler as set forth in claim 1, wherein:
   (a) the percentage by weight of the binder and oils to the weight of the particles is in the range of 10 to 30%.

3. The fragranced particle sampler as set forth in claim 1, wherein:
   (a) the layer contains an emollient substance in the amount of up to 10% by weight of the particles of powder.

4. The fragranced particle sampler s set forth in claim 1, wherein:
   (a) the fragrance powder makes up approximately 80% by weight of the overall layer composition,
   (b) the coating and fragrance oils make up approximately 16% by weight of the overall layer composition, and
   (c) the binder materials constitute approximately 4% by weight of the overall layer composition.

5. A fragranced particle sampler as set forth in claim 1, wherein:
   (a) a coating of a suitable polymeric resin directly beneath the fragranced powder layer to aid in sealing in the fragrance.

6. A printable liquid ink composition to be applied to a smooth surface substrate, comprising:
   (a) a fragranced powder having been enhanced by fragrance oil sealed by a high molecular weight oil/wax, the powder being approximately 30 to 50% by weight of the mixture,
   (b) a liquid volatizing agent constituting by weight of from 40 to 85% of the mixture for providing a liquid suspension medium prior to application of the ink and drying thereof, and
   (c) binder and emollient material forming by weight from 0.25 to 7% by weight of the mixture.

7. The fragrance particle sampler of claim 1, wherein:

(a) the adhesion/cohesion promoting substance is selected from the group consisting of fatty esters, fatty alcohol, and fatty acids.

8. The fragrance particle sampler of claim 1, wherein:
   (a) the discrete free-flowing separate particles are equivalent in size when removed from the substrate surface by light finger pressure as they were prior to being mixed with the binding material.

9. The method of producing a thin, flat fragrance sampler having a thin removable dry powder layer, comprising the steps of:
   (a) coating a fragrance powder with a high molecular weight sealing oil/wax constituting a percentage by weight which is very substantially less than that of the fragranced powder,
   (b) mixing the coated fragrance powder with a liquid volatizing agent which constitutes a greater percent by weight of the mixture than the weight of the coated powder,
   (c) applying the mixture in volatile liquid form to form a substrate having a coated surface, and
   (d) drying the fragranced powder layer applied to the substrate to obtain a dry readily removable layer of discrete fragrance powder particles equivalent in size to the fragrance powder particles prior to coating.

* * * * *